United States Patent
Williams-Harry et al.

(10) Patent No.: US 10,457,767 B2
(45) Date of Patent: Oct. 29, 2019

(54) METHOD OF PREPARING A POLYCARBODIIMIDE POLYMER AND POLYCARBODIIMIDE POLYMER PREPARED THEREBY

(71) Applicant: BASF SE, Ludwigshafen (DE)

(72) Inventors: Michele Williams-Harry, Northville, MI (US); Rajesh Kumar, Riverview, MI (US)

(73) Assignee: BASF SE, Ludwigshafen am Rhein (DE)

( * ) Notice: Subject to any disclaimer, the term of this patent is extended or adjusted under 35 U.S.C. 154(b) by 27 days.

(21) Appl. No.: 15/118,147

(22) PCT Filed: Feb. 12, 2015

(86) PCT No.: PCT/US2015/015616
§ 371 (c)(1),
(2) Date: Aug. 11, 2016

(87) PCT Pub. No.: WO2015/123416
PCT Pub. Date: Aug. 20, 2015

(65) Prior Publication Data
US 2017/0166678 A1 Jun. 15, 2017

Related U.S. Application Data

(60) Provisional application No. 61/940,049, filed on Feb. 14, 2014.

(51) Int. Cl.
| | | |
|---|---|---|
| *C08G 18/02* | (2006.01) | |
| *C07C 267/00* | (2006.01) | |
| *C07C 271/28* | (2006.01) | |
| *C08G 18/76* | (2006.01) | |
| *C08G 18/09* | (2006.01) | |
| *C08G 18/28* | (2006.01) | |
| *C08G 18/38* | (2006.01) | |
| *C08G 18/71* | (2006.01) | |

(52) U.S. Cl.
CPC .......... *C08G 18/025* (2013.01); *C07C 267/00* (2013.01); *C07C 271/28* (2013.01); *C08G 18/095* (2013.01); *C08G 18/2815* (2013.01); *C08G 18/2865* (2013.01); *C08G 18/3876* (2013.01); *C08G 18/71* (2013.01); *C08G 18/76* (2013.01); *C08G 18/7621* (2013.01)

(58) Field of Classification Search
CPC .. C08G 18/025; C08G 18/76; C08G 18/3876; C08G 18/71; C08G 18/095; C08G 18/2865; C08G 18/2815; C08G 18/7621; C07C 267/00; C07C 271/28
See application file for complete search history.

(56) References Cited

U.S. PATENT DOCUMENTS

| | | | |
|---|---|---|---|
| 2,840,589 A | 6/1958 | Smeltz | |
| 3,056,835 A | 10/1962 | Monagle, Jr. et al. | |
| 3,152,131 A | 10/1964 | Heberling, Jr. | |
| 3,267,137 A | 8/1966 | Fischer | |
| 3,406,197 A | 10/1968 | Ulrich | |
| 3,406,198 A | 10/1968 | Budnick | |
| 3,522,303 A | 7/1970 | Ulrich | |
| 4,085,140 A * | 4/1978 | Ibbotson | C08G 18/025 540/202 |
| 4,143,063 A | 3/1979 | Alberino et al. | |
| 4,587,301 A | 5/1986 | Watson, Jr. et al. | |
| 4,820,863 A | 4/1989 | Taylor | |
| 5,047,588 A | 9/1991 | Taylor | |
| 5,081,173 A | 1/1992 | Taylor | |
| 5,574,083 A | 11/1996 | Brown et al. | |
| 6,111,017 A * | 8/2000 | Imashiro | C08G 18/025 525/123 |
| 7,258,921 B2 | 8/2007 | Hashiba et al. | |

FOREIGN PATENT DOCUMENTS

| | | |
|---|---|---|
| DE | 1 122 057 B | 1/1962 |
| EP | 0 628 582 A2 | 12/1994 |
| EP | 0 531 803 B1 | 6/1995 |
| EP | 0 881 243 A1 | 12/1998 |
| EP | 1 054 029 A1 | 11/2000 |
| WO | WO 2009/120559 A1 | 10/2009 |
| WO | WO 2013/033186 A1 | 3/2013 |

OTHER PUBLICATIONS

International Search Report for Application No. PCT/US2015/015616 dated May 22, 2015, 3 pages.
Chen, An-Liu et al., "Well-Defined Polyamide Synthesis from Diisocyanates and Diacids Involving Hindered Carbodiimide Intermediates", American Chemical Society, Macromolecules 2011, 44, pp. 46-59.
English language abstract not found for DE 1 122 057; however, see English language equivalent U.S. Pat. No. 3,267,137. Original document extracted from espacenet.com database on Sep. 8, 2016, 4 pages.
Bell, Stephen A. et al., "Catalytic Double-Bond Metathesis without the Transition Metal", *J. Am. Chem. Soc.*, 2002, vol. 124, pp. 10698-10705.

(Continued)

*Primary Examiner* — Rabon A Sergent
(74) *Attorney, Agent, or Firm* — DLA Piper LLP (US)

(57) ABSTRACT

A method of producing a polycarbodiimide polymer comprises heating a precursor compound at a desired temperature. The method further comprises combining the precursor compound, a diisocyanate compound, and a carbodiimidization catalyst to form a reaction mixture. Finally, the method comprises heating the reaction mixture for a first period of time at a first temperature, thereby reacting the precursor compound and the diisocyanate compound in the presence of the carbodiimidization catalyst to produce the polycarbodiimide polymer.

17 Claims, No Drawings

(56) References Cited

OTHER PUBLICATIONS

Campbell, Tod W. et al., "Carbodiimides. I. Concervsion of Isocyanates to Carbodiimides with Phospholine Oxide Vatalyst", *Journal of the American Chemical Society*, 84, vol. 19, Oct. 5, 1962, pp. 3673-3677.

Bell, Stephen A. et al., "Iminophosphorane-mediated carbodiimide metathesis", *Chem. Commun.*, Jul. 5, 2000, pp. 1375-1376.

Monagle, John. J., "Carbodiimides. III. Conversion of Isocyanates to Carbodiimides. Catalyst Studies", *The Journal of Organic Chemistry* 27, vol. 11, Nov. 1962, pp. 3851-3855.

Williams-Harry, Dr. Michele, "Polycarbodiimide Hardener Synthesis and Formulation with Acid Functional Resins", *BASF Polyurethane PM R&D Report*, Ref.-No. 418990, Mar. 13, 2015, 14 pages.

\* cited by examiner

000
METHOD OF PREPARING A POLYCARBODIIMIDE POLYMER AND POLYCARBODIIMIDE POLYMER PREPARED THEREBY

CROSS-REFERENCE TO RELATED APPLICATIONS

This application is the National Stage of International Patent Application No. PCT/US2015/015616, filed on Feb. 12, 2015, which claims priority to and all the advantages of U.S. Provisional Patent Application No. 61/940,049, filed on Feb. 14, 2014, the content of which is incorporated herein by reference.

FIELD OF THE INVENTION

The present invention generally relates to a method of producing a polycarbodiimide polymer and, more specifically, to a method of producing a polycarbodiimide polymer having a low variation in molecular weight distribution and which results in fewer byproducts.

DESCRIPTION OF THE RELATED ART

Polycarbodiimides and compositions including polycarbodiimides are generally known in the art. Polycarbodiimides include repeating structuring units represented by —(N=C=N)$_n$—, where subscript n designates the number of times this structural unit is repeated in the polycarbodiimides.

Methods of producing polycarbodiimides are also known in the art. In conventional methods of producing polycarbodiimides, an organic diisocyanate, such as an aromatic diisocyanate, is polymerized in the presence of a carbodiimidization catalyst. Generally, the organic diisocyanate is polymerized in the presence of the carbodiimidization catalyst while disposed in a solvent such that the polycarbodiimide is produced in solution.

However, in conventional methods of producing polycarbodiimides in solution, the polycarbodiimides precipitate and/or gel in the solvent once the polycarbodiimides reach a certain molecular weight, which is typically from 1,000 to 3,000. Once the polycarbodiimides precipitate and/or gel in the solvent, polymerization generally ceases such that the molecular weight of the polycarbodiimide does not increase. As such, polycarbodiimides produced via conventional methods have relatively low molecular weight, which significantly decreases potential applications in which the polycarbodiimides may be utilized in view of the physical properties obtainable from such polycarbodiimides.

Other alternative conventional methods have been utilized to increase the molecular weight of polycarbodiimides. However, these alternative conventional methods generally result in polycarbodiimides having high variation in the molecular weight distribution. This broad dispersity of polycarbodiimides produced via these methods renders such polycarbodiimides undesirable for many applications, such as coatings and inks. Further, such polycarbodiimides prepared via conventional methods generally have undesirable stability.

SUMMARY OF THE INVENTION AND ADVANTAGES

The present invention provides a method of producing a polycarbodiimide polymer. The method comprises heating a precursor compound at a desired temperature. The method further comprises combining the precursor compound, a diisocyanate compound, and a carbodiimidization catalyst to form a reaction mixture. Finally, the method comprises heating the reaction mixture for a first period of time at a first temperature, thereby reacting the precursor compound and the diisocyanate compound in the presence of the carbodiimidization catalyst to produce the polycarbodiimide polymer.

The method of the present invention produces polycarbodiimide polymers having excellent physical properties and is suitable for diverse applications. Moreover, the polycarbodiimide polymers produced via the method have a desirably narrow variation in molecular weight distribution, which provides for repeatable and reproducible qualities and characteristics of polycarbodiimide polymers, and excellent stability.

DETAILED DESCRIPTION OF THE INVENTION

The present invention provides a method of producing a polycarbodiimide polymer and the polycarbodiimide polymer produced thereby. The polycarbodiimide polymer of the present invention has excellent physical properties and is suitable for use in diverse applications, as described in greater detail below. For example, the polycarbodiimide polymer may be utilized in synthetic fiber applications, automotive applications, aerospace applications, coating compositions, inks, and/or electronic applications. However, it is to be appreciated that the polycarbodiimide polymer is not limited to such applications; for example, the polycarbodiimide polymer of the present invention may be utilized in other applications where performance polymers are typically utilized.

The method comprises heating a precursor compound at a desired temperature. In various embodiments, the precursor compound comprises a carbodiimide compound, a urethane compound, a thiourethane compound, or a urea compound. The precursor compound may alternatively comprise a combination of two or more of these compounds, which may result in polycarbodiimide polymers having different substituents or functionalities. The precursor compound may be synthesized in the method or may be otherwise obtained or supplied, e.g. the precursor compound may be off-the-shelf. When the precursor compound is synthesized in the method, the precursor compound is typically formed from an initial compound, and the method further comprises the step of preparing the precursor compound from the initial compound at the desired temperature. In these embodiments, the precursor compound is generally formed from the initial compound prior to combining all components simultaneously to prepare the polycarbodiimide polymer, in contrast to conventional methods. For example, in conventional methods, all of the components are combined simultaneously, rather than discretely forming a precursor compound from an initial compound. This results in the production of many undesirable byproducts and difficulty in controlling molecular weight distribution of the conventional polycarbodiimide polymer. However, in the instant method, when the precursor compound is first formed from the initial compound, the production of undesirable byproducts is minimized and increased control over the molecular weight distribution of the polycarbodiimide polymer is realized.

For example, the precursor compound typically comprises a dimer of at least the initial compound. When the precursor compound is the dimer, the sub-units of the dimer are generally linked via a carbodiimide bond. In particular, each precursor compound generally contains a single carbodiimide bond, with sub-units of the dimer, which comprise or are formed from the initial compound, be linked via the single carbodiimide bond. Formation of the precursor compound may be monitored in real time via infrared or other spectroscopy methods. Specific examples of suitable precursor compounds, as well as specific examples of initial compounds suitable for forming the precursor compounds, are described in turn below.

For example, in certain embodiments, the precursor compound comprises the carbodiimide compound. In these embodiments, the precursor compound may have the general formula R—N═C═N—R, where each R is an independently selected organic group. For example, R may be aromatic, aliphatic, cyclic, alicyclic, etc. When the precursor compound comprises the carbodiimide compound, there is generally but one carbodiimide linkage in the precursor compound. In addition, in these embodiments, the precursor compound is monomeric in nature, as opposed to being an oligomeric or polymeric carbodiimide compound.

Typically, R is an aromatic group such that the carbodiimide compound has two aromatic functional groups. One specific embodiment of such a carbodiimide compound is reproduced below for illustrative purposes only:

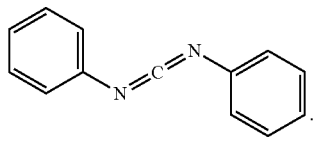 [SMILES: C(=Nc1ccccc1)=Nc1ccccc1]

As introduced above, the precursor compound may be formed from an initial compound. In embodiments where the precursor compound comprises the carbodiimide compound, and when the carbodiimide compound is formed from the initial compound, the initial compound typically comprises a monofunctional isocyanate. The monofunctional isocyanate may be aromatic or aliphatic and contains a single isocyanate functional group. One specific example of a monofunctional isocyanate suitable for the purposes of the initial compound, i.e., suitable for forming the precursor compound, is phenyl isocyanate, which is reproduced immediately below for illustrative purposes only:

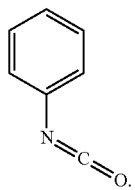

Combinations of different types of monofunctional isocyanates may be utilized as the initial compound.

In this embodiment, the initial compound may be utilized to form the precursor compound via a carbodiimidization reaction. In particular, the initial compound may be reacted in the presence of a carbodiimidization catalyst. Specific examples of suitable carbodiimidization catalysts are described in greater detail below with reference to the method. If desired, the initial compound may also be reacted in the presence of a stabilizing agent. For example, in various embodiments, the stabilizing agent comprises triphenylphosphite, 2,6-di-tert-butyl-4-methylphenol, a variation thereof, or combinations thereof. The precursor compound is generally formed at the desired temperature. As such, when the precursor compound is prepared from the initial compound in the method, the precursor compound is generally heated at the desired temperature upon its formation.

For example, when the initial compound comprises the monofunctional isocyanate, the precursor compound formed therefrom is formed by effectively dimerizing the monofunctional isocyanate. Said differently, two monofunctional isocyanates react to form the carbodiimide compound, with the carbodiimide linkage in the carbodiimide compound being formed the isocyanate groups of the two monofunctional isocyanates. A reaction scheme illustrating the reaction to form the precursor compound from the initial compound when the initial compound is phenyl isocyanate is below:

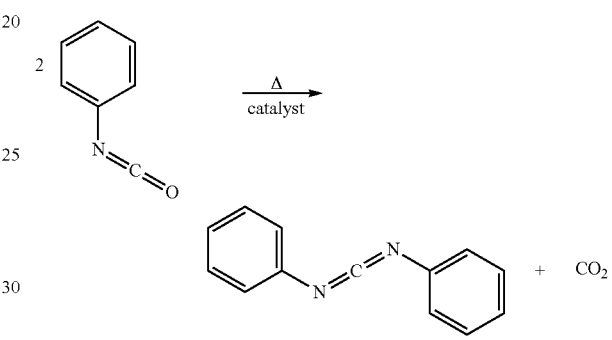

In other embodiments, the precursor compound comprises the urethane compound. In these embodiments, the precursor compound comprises at least one, typically two, urethane linkages (or carbamate ester groups), which have the general formula $RNHCO_2R$, where each R is an independently selected organic group. For example, R may be aromatic, aliphatic, cyclic, alicyclic, etc. When the precursor compound comprises the urethane compound, there is generally but one carbodiimide linkage in the precursor compound. When the precursor compound comprises the urethane compound, the urethane compound is generally monomeric in nature, as opposed to being an oligomeric or polymeric urethane compound.

One specific embodiment of such a urethane compound is reproduced below for illustrative purposes only:

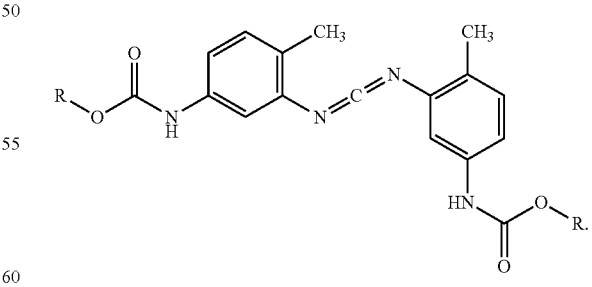

As readily understood in the art, the urethane compound above is merely one exemplary example, and the structure of the urethane compound utilized may vary based on a variety of factors, including methods of its preparation. In the structure above, each R is an independently selected organic group. In certain embodiments, R is a hydrocarbyl group having from 1 to 20, alternatively from 1 to 15, alternatively from 1 to 10, carbon atoms. R is typically an alkyl group.

As introduced above, the precursor compound may be formed from an initial compound. In embodiments where the precursor compound comprises the urethane compound, and when the urethane compound is formed from the initial compound, the initial compound typically comprises a monofunctional alcohol. The monofunctional alcohol may be aromatic or aliphatic and contains a single hydroxyl functional group. Typically, the monofunctional alcohol is aliphatic and linear or branched. Further, the monofunctional alcohol is typically a primary alcohol. In these embodiments, specific examples of suitable monofunctional alcohols include $C_1$-$C_{20}$ alcohols, such as methanol, ethanol, n-propanol, n-butanol, n-hexanol, n-heptanol, n-octanol, n-nonanol, n-decanol, 2-ethylhexanol, etc. Combinations of different types of monofunctional alcohols may be utilized as the initial compound. When different types of monofunctional alcohols are utilized as the initial compound, the precursor compound may not be in dimer form considering the different R groups associated with different types of monofunctional alcohols.

In this embodiment, the initial compound may be utilized to form the precursor compound via a step-wise reaction. In particular, the initial compound may be reacted with a diisocyanate compound to form an intermediate compound. The intermediate compound generally contains one isocyanate group. The intermediate compound may then be effectively dimerized to form the precursor compound. Specific examples of suitable diisocyanate compounds are described in greater detail below with reference to the method.

One specific example of a diisocyanate compound suitable for the method is toluene diisocyanate (TDI). When the initial compound comprises the monofunctional alcohol and the intermediate compound is formed from the initial compound and TDI, one exemplary reaction scheme is illustrated below:

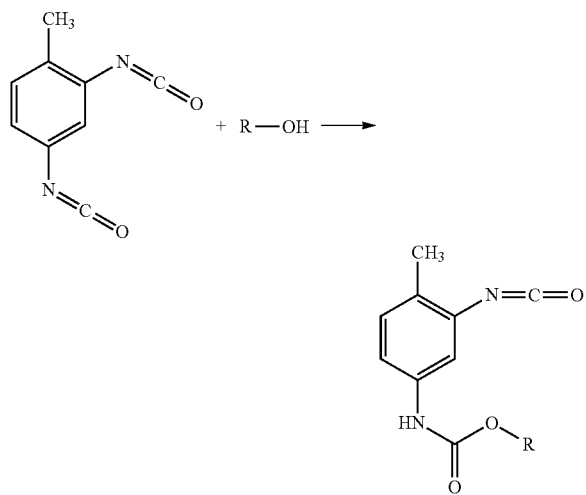

In this embodiment, the intermediate compound formed from the initial compound may be utilized to form the precursor compound via a carbodiimidization reaction. In particular, the intermediate compound may be reacted in the presence of a carbodiimidization catalyst. Specific examples of suitable carbodiimidization catalysts are described in greater detail below with reference to the method. If desired, the intermediate compound may also be reacted in the presence of a stabilizing agent. In various embodiments, the stabilizing agent comprises triphenylphosphite, 2,6-di-tert-butyl-4-methylphenol, a variation thereof, or combinations thereof. The precursor compound is generally formed at the desired temperature. As such, when the precursor compound is prepared from the intermediate compound in the method, the precursor compound is generally heated at the desired temperature upon its formation.

For example, when the initial compound comprises the monofunctional alcohol, the precursor compound ultimately formed therefrom is formed by effectively dimerizing the intermediate compound formed from monofunctional alcohol. Said differently, two intermediate compounds react to form the urethane compound, with the carbodiimide linkage in the urethane compound being formed from the isocyanate groups of the two intermediate compounds. A sample reaction scheme illustrating the reaction to form the precursor compound from the intermediate compound, when the intermediate compound is formed from the monofunctional alcohol and TDI, is below:

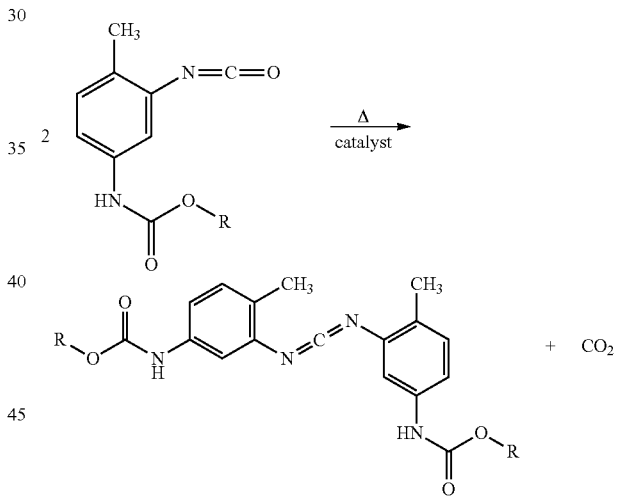

In other embodiments, the precursor compound comprises the thiourethane compound. In these embodiments, the precursor compound comprises at least one, typically two, thiourethane linkages, which have the general formula RNHCOSR, where each R is an independently selected organic group. For example, R may be aromatic, aliphatic, cyclic, alicyclic, etc. When the precursor compound comprises the thiourethane compound, there is generally but one carbodiimide linkage in the precursor compound. When the precursor compound comprises the thiourethane compound, the thiourethane compound is generally monomeric in nature, as opposed to being an oligomeric or polymeric thiourethane compound.

One specific embodiment of such a thiourethane compound is reproduced below for illustrative purposes only:

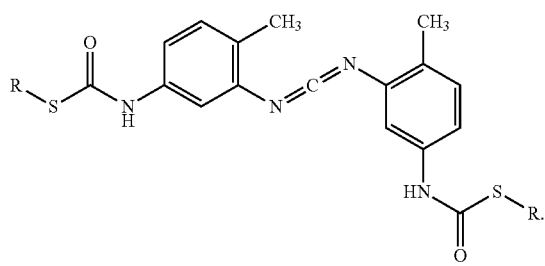
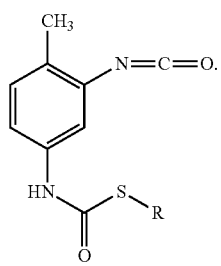

As readily understood in the art, the thiourethane compound above is merely one exemplary example, and the structure of the thiourethane compound utilized may vary based on a variety of factors, including methods of its preparation. In the structure above, each R is an independently selected organic group. In certain embodiments, R is a hydrocarbyl group having from 1 to 20, alternatively from 1 to 15, alternatively from 1 to 10, carbon atoms. R is typically an alkyl group.

As introduced above, the precursor compound may be formed from an initial compound. In embodiments where the precursor compound comprises the thiourethane compound, and when the thiourethane compound is formed from the initial compound, the initial compound typically comprises a monofunctional thiol. The monofunctional alcohol may be aromatic or aliphatic and contains a single sulfhydryl functional group. Typically, the monofunctional thiol is aliphatic and linear or branched. Further, the monofunctional thiol is typically a primary thiol. In these embodiments, specific examples of suitable monofunctional thiols include $C_1$-$C_{20}$ thiols, such as methanethiol, ethanethiol, propanethiol, butanethiol, hexanethiol, heptanethiol, octanethiol, nonanethiol, decanethiol, etc. Combinations of different types of monofunctional thiols may be utilized as the initial compound. When different types of monofunctional thiols are utilized as the initial compound, the precursor compound may not be in dimer form considering the different R groups associated with different types of monofunctional thiols.

In this embodiment, the initial compound may be utilized to form the precursor compound via a step-wise reaction. In particular, the initial compound may be reacted with a diisocyanate compound to form an intermediate compound. The intermediate compound generally contains one isocyanate group. The intermediate compound may then be effectively dimerized to form the precursor compound. Specific examples of suitable diisocyanate compounds are described in greater detail below with reference to the method.

One specific example of a diisocyanate compound suitable for the method is toluene diisocyanate (TDI). When the initial compound comprises the monofunctional alcohol and the intermediate compound is formed from the initial compound and TDI, one exemplary reaction scheme is illustrated below:

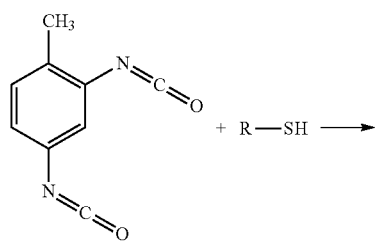

In this embodiment, the intermediate compound formed from the initial compound may be utilized to form the precursor compound via a carbodiimidization reaction. In particular, the intermediate compound may be reacted in the presence of a carbodiimidization catalyst. Specific examples of suitable carbodiimidization catalysts are described in greater detail below with reference to the method. If desired, the intermediate compound may also be reacted in the presence of a stabilizing agent. In various embodiments, the stabilizing agent comprises triphenylphosphite, 2,6-di-tert-butyl-4-methylphenol, a variation thereof, or combinations thereof. The precursor compound is generally formed at the desired temperature. As such, when the precursor compound is prepared from the intermediate compound in the method, the precursor compound is generally heated at the desired temperature upon its formation.

For example, when the initial compound comprises the monofunctional thiol, the precursor compound ultimately formed therefrom is formed by effectively dimerizing the intermediate compound formed from the monofunctional thiol. Said differently, two intermediate compounds react to form the thiourethane compound, with a carbodiimide linkage in the thiourethane compound being formed from the isocyanate groups of the two intermediate compounds. A sample reaction scheme illustrating the reaction to form the precursor compound from the intermediate compound, when the intermediate compound is formed from the monofunctional thiol and TDI, is below:

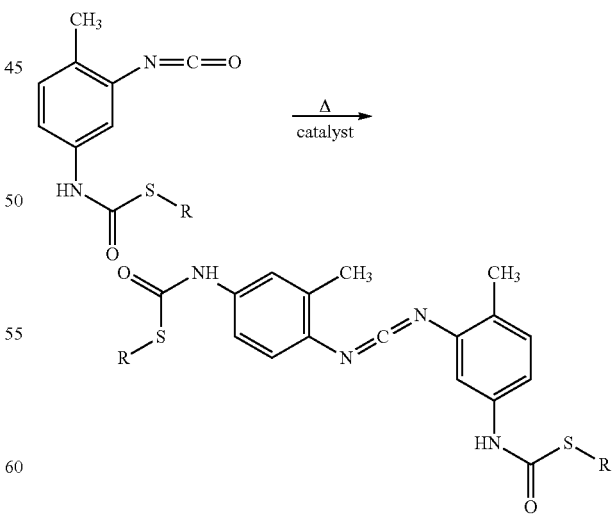

In other embodiments, the precursor compound comprises the urea compound. In these embodiments, the precursor compound comprises at least one, typically two, carbamide linkages, which have the general formula $CO(NR^1H)_2$, where each $R^1$ is independently H or an independently selected organic group. For example, R may be aromatic, aliphatic, cyclic, alicyclic, etc. When the precursor compound comprises the urea compound, there is generally but one carbodiimide linkage in the precursor compound. When the precursor compound comprises the urea compound, the urea compound is generally monomeric in nature, as opposed to being an oligomeric or polymeric urea compound.

One specific embodiment of such a urea compound is reproduced below for illustrative purposes only:

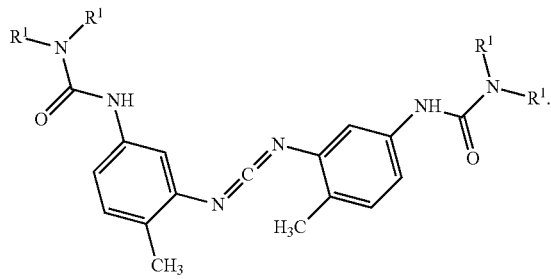

As readily understood in the art, the urea compound above is merely one exemplary example, and the structure of the urea compound utilized may vary based on a variety of factors, including methods of its preparation. In the structure above, each $R^1$ is independently H or an independently selected organic group. In certain embodiments when $R^1$ is the organic group, $R^1$ is a hydrocarbyl group having from 1 to 20, alternatively from 1 to 15, alternatively from 1 to 10, carbon atoms.

As introduced above, the precursor compound may be formed from an initial compound. In embodiments where the precursor compound comprises the urea compound, and when the urea compound is formed from the initial compound, the initial compound typically comprises an amine compound. The amine compound may be primary or secondary, i.e., the amine compound may include one NH bond or two NH bonds. The amine compound may be aliphatic, aromatic, or comprise different types of amine compounds that are independently aliphatic and/or aromatic. The amine compound may be bulky or sterically hindered, e.g. the amine compound may comprise a sterically hindered primary amine. In these embodiments, the amine compound typically includes at least one branched or aromatic substituent.

Specific examples of suitable amine compounds include tertiary butyl amine, dibutylamine, dicyclohexylamine, diphenyl amine, etc. Combinations of different types of amine compounds may be utilized as the initial compound. When different types of amine compounds are utilized as the initial compound, the precursor compound may not be in dimer form considering the different substituents associated with different types of amine compounds.

In this embodiment, i.e., when the precursor compound is formed from the amine compound, the initial compound may be utilized to form the precursor compound via a step-wise reaction. In particular, the initial compound may be reacted with a diisocyanate compound to form an intermediate compound. The intermediate compound generally contains one isocyanate group. The intermediate compound may then be effectively dimerized to form the precursor compound. Specific examples of suitable diisocyanate compounds are described in greater detail below with reference to the method.

One specific example of a diisocyanate compound suitable for the method is toluene diisocyanate (TDI). When the initial compound comprises the monofunctional alcohol and the intermediate compound is formed from the initial compound and TDI, one exemplary reaction scheme is illustrated below:

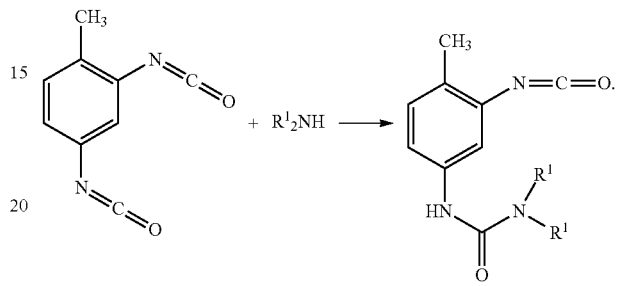

In this embodiment, the intermediate compound formed from the initial compound may be utilized to form the precursor compound via a carbodiimidization reaction. In particular, the intermediate compound may be reacted in the presence of a carbodiimidization catalyst. Specific examples of suitable carbodiimidization catalysts are described in greater detail below with reference to the method. If desired, the intermediate compound may also be reacted in the presence of a stabilizing agent. In various embodiments, the stabilizing agent comprises triphenylphosphite, 2,6-di-tert-butyl-4-methylphenol, a variation thereof, or combinations thereof. The precursor compound is generally formed at the desired temperature. As such, when the precursor compound is prepared from the intermediate compound in the method, the precursor compound is generally heated at the desired temperature upon its formation.

For example, when the initial compound comprises the amine compound, the precursor compound ultimately formed therefrom is formed by effectively dimerizing the intermediate compound formed from the amine compound. Said differently, two intermediate compounds react to form the urea compound, with a carbodiimide linkage in the urea compound being formed from the isocyanate groups of the two intermediate compounds. A sample reaction scheme illustrating the reaction to form the precursor compound from the intermediate compound, when the intermediate compound is formed from the amine compound and TDI, is below:

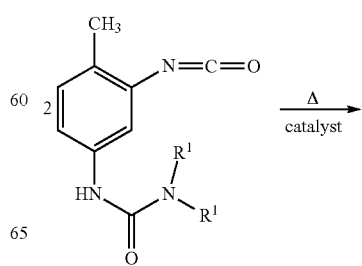

-continued

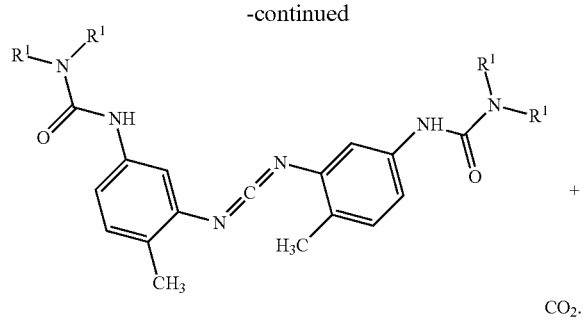

$CO_2$.

In the embodiments described above in which the precursor compound is formed form the initial compound, the components utilized to form the precursor compound may be combined in various orders or simultaneously. Typically, when the initial compound is reacted with the diisocyanate compound, the diisocyanate compound is heated at the desired temperature prior to addition of the initial compound to form the precursor compound.

Regardless of the particular precursor compound utilized, and regardless of whether the precursor compound is formed from the initial compound, the method comprises heating the precursor compound at the desired temperature. The desired temperature is typically from 70 to 150° C. Heating the precursor compound at the desired temperature may be carried out in the presence of a solvent or in the absence of a solvent. If desired, suitable solvents include organic solvents, such as toluene, xylene, tetrahydrofuran, etc. However, in certain embodiments, heating the precursor compound is carried out in the absence of any solvent other than the precursor compound, the carbodiimidization catalyst, and any residual amounts of the initial compound and/or intermediate compound. Typically, the method comprises forming the precursor compound from the initial compound in situ at the desired temperature.

When the method comprises forming the precursor compound from the initial compound, the precursor compound is typically formed in an inert atmosphere, i.e., an atmosphere substantially free from oxygen. Any inert atmosphere known in the art may be utilized during the step of heating the reaction mixture. Typically, the inert atmosphere comprises an inert gas, such as nitrogen, argon, helium, and carbon dioxide, etc.

The method further comprises combining the precursor compound, a diisocyanate compound, and a carbodiimidization catalyst to form a reaction mixture.

In various embodiments, the step of heating the precursor compound at the desired temperature is carried out in the absence of the diisocyanate compound, although a diisocyanate compound may be utilized to form the precursor compound, as described above. Said differently, when the method comprises preparing the precursor compound from the initial compound, the precursor compound is generally formed before combining with the diisocyanate compound to form the polycarbodiimide polymer. More specifically, in certain embodiments, the diisocyanate compound utilized to form the precursor compound, if any, is fully consumed such that there are no residual amounts of the diisocyanate compound present along with the precursor compound at the time of its formation. In these embodiments when the diisocyanate compound is also utilized to form the precursor compound, an additional amount of the diisocyanate compound is utilized in the method and combined with the precursor compound to form the polycarbodiimide polymer.

In the instant method, the precursor compound is obtained and utilized or formed in situ prior to forming the polycarbodiimide polymer. This is distinguished from conventional methods, where various reactants are combined together in a single step so as to form conventional polycarbodiimides. For example, the instant method is distinguished from conventional methods which may merely combine the diisocyanate compound and a carbodiimidization catalyst, optionally in combination with a capping agent, such as phenyl isocyanate. More specifically, in such conventional methods, it is difficult or impossible to control capping of the conventional polycarbodiimide as it is formed, which in turn makes it difficult or impossible to control the molecular weight distribution of the conventional polycarbodiimides formed via conventional methods. In contrast, in the instant method, the precursor compound generally already includes a carbodiimide linkage, and the polycarbodiimide polymer is grown at this carbodiimide linkage. As such, the precursor compound is ultimately utilized to cap each terminal of the polycarbodiimide polymer, as described in greater detail below. Capping with the precursor compound provides certain advantages relative to the ability to control the molecular weight of the polycarbodiimide polymer, which reduces variations in molecular weight distribution. The instant method also greatly reduces undesirable byproducts associated with conventional methods, such as urea linkages, guanidine branched structures, and/or uretone imines. This can be readily confirmed via gel permeation chromatography or other spectroscopy methods.

The diisocyanate compound includes two isocyanate-functional groups and may be aliphatic, aromatic, or combinations thereof. Specific examples of aliphatic diisocyanate compounds include isophorone diisocyanates (IPDI), hexamethylene diisocyanates (HDI), dicyclohexylmethane diisocyanates (HMDI), cyclohexyl diisocyanates (CHDI), tetramethylxylene diisocyanates (TMXDI), and combinations thereof, as well as any isomers of these aliphatic diisocyanate compounds. Typically, however, the diisocyanate compound comprises an aromatic diisocyanate compound.

Specific examples of aromatic diisocyanate compounds include diphenylmethane diisocyanates (MDI), polymeric diphenylmethane diisocyanates (pMDI), toluene diisocyanates (TDI), naphthalene diisocyanates (NDI), tolidine diisocyanates (TODI), and combinations thereof, as well as any isomers of these aromatic diisocyanate compounds. In certain embodiments when the diisocyanate compound comprises the aromatic diisocyanate compound, the diisocyanate compound has an ortho-substituted isocyanate group. Ortho-substitution in the diisocyanate compound generally improves stability of the polycarbodiimide polymer formed via the method.

In certain embodiments, the diisocyanate compound comprises toluene diisocyanate (TDI). In these embodiments, the diisocyanate compound may comprise either isomer of toluene diisocyanate (TDI), i.e., the diisocyanate compound may comprise 2,4-toluene diisocyanate (2,4-TDI) or 2,6-toluene diisocyanate (2,6-TDI). Alternatively, the diisocyanate compound may comprise a blend of these isomers, i.e., the diisocyanate compound may comprise both 2,4-toluene diisocyanate (2,4-TDI) and 2,6-toluene diisocyanate (2,6-TDI). One specific example of a commercially available diisocyanate compound suitable for the purposes of the present invention is Lupranate® T-80, which is commercially available from BASF Corporation of Florham Park, N.J. Notably, Lupranate® T-80 comprises a blend of 2,4-toluene diisocyanate (2,4-TDI) and 2,6-toluene diisocyanate (2,6-TDI). In certain embodiments, the diisocyanate compound consists essentially of, alternatively consists of, TDI. Generally, the diisocyanate compound comprises TDI in an amount of from greater than 95, alternatively greater than 96, alternatively greater than 97, alternatively greater than 98, alternatively greater than 99, percent by weight based on the total weight of isocyanate present in the diisocyanate compound. Alternatively, the diisocyanate compound may comprise methylene diphenyl diisocyanate (MDI). Suitable isomers thereof include 2,2'-MDI, 2,4'-MDI, 4,4'-MDI, and combinations thereof. Combinations of different types of diisocyanate compounds may be utilized, e.g. MDI in combination with TDI.

The carbodiimidization catalyst may be any type of carbodiimidization catalyst known to those skilled in the art for producing a polycarbodiimide. Generally, the carbodiimidization catalyst is selected from the group of tertiary amides, basic metal compounds, carboxylic acid metal salts and/or non-basic organo-metallic compounds. In certain embodiments, the carbodiimidization catalyst comprises a phosphorus compound.

Specific examples of phosphorus compounds suitable for the purposes of the carbodiimidization catalyst include, but are not limited to, phospholene oxides such as 3-methyl-1-phenyl-2-phospholene oxide, 1-phenyl-2-phospholen-1-oxide, 3-methy-1-2-phospholen-1-oxide, 1-ethyl-2-phospholen-1-oxide, 3-methyl-1-phenyl-2-phospholen-1-oxide, and 3-phospholene isomers thereof. A particularly suitable phospholene oxide is 3-methyl-1-phenyl-2-phospholene oxide. For illustrative purposes only, 3-methyl-1-phenyl-2-phospholene oxide is represented by the following structure:

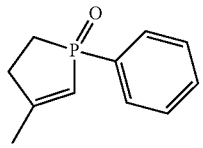

Additional examples of phosphorous compounds suitable for the purposes of the carbodiimidization catalyst include, but are not limited to, phosphates, diaza- and oxaza phospholenes and phosphorinanes. Specific examples of such phosphorous compounds include, but are not limited to, phosphate esters and other phosphates such as trimethyl phosphate, triethyl phosphate, tributyl phosphate, tri-2-ethylhexyl phosphate, tributoxyethyl phosphate, trioleyl phosphate, triphenyl phosphate, tricresyl phosphate, trixylenyl phosphate, cresyl diphenyl phosphate, xylenyl diphenyl phosphate, 2-ethylhexyldiphenyl phosphate, and the like; acidic phosphates such as methyl acid phosphate, ethyl acid phosphate, isopropyl acid phosphate, butyl acid phosphate, 2-ethylhexyl acid phosphate, isodecyl acid phosphate, lauryl acid phosphate, isotridecyl acid phosphate, myristyl acid phosphate, isostearyl acid phosphate, oleyl acid phosphate, and the like; tertiary phosphites such as triphenyl phosphite, tri(p-cresyl) phosphite, tris(nonylphenyl) phosphite, tri-isooctyl phosphite, diphenyisodecyl phosphite, phenyldiisodecyl phosphite, triisodecyl phosphite, tristearyl phosphite, trioleyl phosphite, and the like; secondary phosphites such as di-2-ethylhexyl hydrogen phosphite, dilauryl hydrogen phosphite, dioleyl hydrogen phosphite, and the like; and phosphine oxides, such as triethylphosphine oxide, tributylphosphine oxide, triphenylphosphine oxide, tris(chloromethyl)phosphine oxide, tris(chloromethyl)phosphine oxide, and the like. Carbodiimidization catalysts comprising phosphate esters and methods for their preparation are described in U.S. Pat. No. 3,056,835, which is hereby incorporated by reference in its entirety.

Yet further examples the carbodiimidization catalyst include, but are not limited to, 1-phenyl-3-methyl phospholene oxide, 1-benzyl-3-methyl phospholene oxide, 1-ethyl-3-methyl phospholene oxide, 1-phenyl-3-methyl phospholene dichloride, 1-benzyl-3-methyl phospholene dichloride, 1-ethyl-3-methyl phospholene dichloride, 1-phenyl-3-methyl phospholene sulphide, 1-phenyl-3-methyl phospholene sulphide, 1-benzyl-3-methyl phospholene sulphide, 1-ethyl-3-methyl phospholene sulphide, 1-phenyl-1-phenylimino-3-methyl phospholene oxide, 1-benzyl-1-phenylimino-3-methyl phospholene oxide 1-ethyl-1-phenylimino-3-methyl phospholene oxide, 1-phenyl phospholidine, 1-benzyl phospholidine, 1-ethyl phospholidine, and 1-phenyl-3-methyl phospholene oxide.

The carbodiimidization catalyst may alternatively comprise diaza- and oxaza-phospholenes and phosphorinanes. Diaza- and oxaza-phospholenes and phosphorinanes and methods for their preparation are described in U.S. Pat. No. 3,522,303, which is hereby incorporated by reference in its entirety. Specific diaza- and oxaza-phospholenes and phosphorinanes include, but are not limited to, 2-ethyl-1,3-dimethyl-1,3,2-diazaphospholane-2-oxide; 2-chloromethyl-1,3-dimethyl-1,3,2-diazaphospholane-2-oxide; 2-trichloromethyl-1,3-dimethyl-1,3,2-diazaphospholane-2-oxide; 2-phenyl-1,3-dimethyl-1,3,2-diazaphospholane-2-oxide; 2-phenyl-1,3-dimethyl-1,3,2-diaza-phosphorinane-2-oxide; 2-benzyl-1,3-dimethyl-1,3,2-diazaphospholane-2-oxide; 2-allyl-1,3-dimethyl-1,3,2-diazaphospholane-2-oxide; 2-bromomethyl-1,3-dimethyl-1,3,2-diazaphospholane-2-oxide; 2-cyclohexyl-1,3-dimethyl-1,3,2-diazaphospholane-2-oxide; 2-(2-ethoxyethyl1,3-dimethyl-1,3,2-diazaphospholane-2-oxide; and 2-naphthyl-1,3-dimethyl-1,3,2-diazaphospholane-2-oxide, triethyl phosphate, hexamethyl phosphoramide, and the like.

The carbodiimidization catalyst may comprise a triaryl arsine. Triaryl arsines and methods for their preparation are described in U.S. Pat. No. 3,406,198, which is hereby incorporated by reference in its entirety. Specific examples of triaryl arsines include, but are not limited to, triphenylarsine, tris(p-tolyl)arsine, tris(p-methoxyphenyl)arsine, tris(p-ethoxyphenyl)arsine, tris(p-chlorophenyl)arsine, tris(p-fluorophenyl)arsine, tris(2,5-xylyl)arsine, tris(p-cyanophenyl) arsine, tris(1-naphthyl)arsine, tris(p-methylmercaptophenyl) arsine, tris(p-biphenylyl)arsine, p-chlorophenyl bis(p-tolyl) arsine, phenyl(p-chlorophenyl)(p-bromophenyl)arsine, and the like. Additional arsine compounds are described in U.S. Pat. No. 4,143,063, which is hereby incorporated by reference in its entirety. Specific examples of such arsine compounds include, but are not limited to, triphenylarsine oxide, triethylarsine oxide, polymer bound arsine oxide, and the like.

Further, the carbodiimidization catalyst may comprise metallic derivatives of acetlyacetone. Metallic derivatives of acetlyacetone and methods are described in U.S. Pat. No. 3,152,131, which is hereby incorporated by reference in its entirety. Specific examples of metallic derivatives of acetlyacetone include, but are not limited to, metallic derivatives of acetylacetone such as the beryllium, aluminum, zirconium, chromium, and iron derivatives.

Additional examples of the carbodiimidization catalyst include metal complexes derived from a d-group transition element and π-bonding ligand selected from the group consisting of carbon monoxide, nitric oxide, hydrocarbylisocyanides, trihydrocarbylphosphine, trihydrocarbylarsine, trihydrocarbylstilbine, and dihydrocarbylsulfide wherein hydrocarbyl in each instance contains from 1 to 12 carbon atoms, inclusive, provided that at least one of the π-bonding ligands in the complex is carbon monoxide or hydrocarbylisocyanide. Such metal complexes and methods for preparation are described in U.S. Pat. No. 3,406,197, which is hereby incorporated by reference in its entirety. Specific examples of metal complexes include, but are not limited to, iron pentacarbonyl, di-iron pentacarbonyl, tungsten hexacarbonyl, molybdenum hexacarbonyl, chromium hexacarbonyl, dimanganese decacarbonyl, nickel tetracarbonyl, ruthenium pentacarbonyl, the complex of iron tetracarbonyl: methylisocyanide, and the like.

The carbodiimidization catalyst may comprise organotin compounds. Specific examples of organotin compounds include, but are not limited to, dibutytin dilaurate, dibutyltin diacetate, dibutyltin di(2-ethylhexanoate), dioctyltin dilaurate, dibutylin maleate, di(n-octyl)tin maleate, bis(dibutylacetoxytin) oxide, bis(dibutyllauroyloxytin) oxide, dibutyltin dibutoxide, dibutyltin dimethoxide, dibutyltin disalicilate, dibutyltin bis(isooctylmaleate), dibutyltin bis(isopropylmaleate), dibutyltin oxide, tributyltin acetate, tributyltin isopropyl succinate, tributyltin linoleate, tributyltin nicotinate, dimethyltin dilaurate, dimethyltin oxide, diotyltin oxide, bis(tributyltin) oxide, diphenyltin oxide, triphenyltin acetate, tri-n-propyltin acetate, tri-n-propyltin laurate and bis(tri-n-propyltin) oxide, dibutyltin dilauryl mercaptide, dibutyltin bis(isooctylmercaptoacetate), bis(triphenyltin)oxide, stannous oxalate, stannous oleate, stannous naphthenate, stannous acetate, stannous butyrate, stannous 2-ethylhexanoate, stannous laurate, stannous palmitate, stannous stearate, and the like. Typical organotin compounds include, but are not limited to, stannous oxalate, stannous oleate and stannous 2-ethylhexanoate, dibutyltin diacetate, dibutyltin dilaurate, dibutyltin dilaurylmercaptide, dibutyltin bis(isooctylmercaptoacetate), dibutyltin oxide, bis (triphenyltin) oxide, and bis(tri-n-butyltin) oxide.

Further, the carbodiimidization catalyst may comprise various organic and metal carbene complexes, titanium(IV) complexes, copper(I) and/or copper(II) complexes.

The precursor compound, the diisocyanate compound, and the carbodiimidization catalyst may be combined in any order and via various methods. For example, in certain embodiments, the carbodiimidization catalyst and the diisocyanate compound are merely added into a vessel in which the precursor compound is being heated at the desired temperature. The carbodiimidization catalyst and the diisocyanate compound may be separately added or added together as a mixture. Because there may be at least some carbodiimidization catalyst present along with the precursor compound, particularly when the precursor compound is formed in situ in the method, addition of the diisocyanate compound may only be required to form the reaction mixture. However, even when there is at least some carbodiimidization catalyst present along with the precursor compound, an additional amount of the carbodiimidization catalyst may be utilized.

The relative amounts of the components of the reaction mixture may vary. In certain embodiments, the total amount of the carbodiimidization catalyst utilized in the reaction mixture is from greater than 0 to 2, alternatively from 0.0001 to 1.5, alternatively from 0.001 to 1.0, alternatively from 0.01 to 0.5, alternatively from 0.05 to 0.25, percent by weight based on the total weight of the reaction mixture. The amount of the carbodiimidization catalyst may vary based on the presence or absence of various optional components. To this end, the values above relate to the reaction mixture that is free from solvent. The precursor compound and the diisocyanate compound are generally utilized in similar amounts and may make up the balance of the reaction mixture (along with any reaction products or partial reaction products from the reaction). The stabilizing agent may be present along with the precursor compound, or an additional amount of the stabilizing agent may be added along with the diisocyanate compound to form the reaction mixture. Generally, if utilized, the stabilizing agent is present in an amount similar to the carbodiimidization catalyst.

The method further comprises heating the reaction mixture for a first period of time at a first temperature, thereby reacting the precursor compound and the diisocyanate compound in the presence of the carbodiimidization catalyst to produce the polycarbodiimide polymer.

The first temperature may be the same as or different from the desired temperature. In certain embodiments, the desired temperature and the first temperature are each independently from 70 to 150° C. When the desired temperature and the first temperature are independently selected from this range, the desired temperature and the first temperature need not have the same value, e.g. the desired temperature may be 75° C. while the first temperature is 140° C.

Generally, the method is carried out in the same vessel. For example, when the method comprises forming the precursor compound, the precursor compound may be formed in the vessel at the desired temperature. Upon formation of the precursor compound, which may be monitored via spectroscopy methods, e.g. IR spectroscopy, the diisocyanate compound may be disposed in the vessel. Alternatively, in certain embodiments, such as when the precursor compound is formed from the initial compound when the initial compound comprises the monofunctional alcohol, the diisocyanate compound may already be present along with the precursor compound. In these embodiments, additional amounts of the diisocyanate compound may be utilized after the formation of the precursor compound. Similarly, the carbodiimidization catalyst may be utilized to form the precursor compound, and either residual amounts of the carbodiimidization catalyst may be sufficient for preparing the polycarbodiimide polymer, or additional amounts of the carbodiimidization catalyst may be utilized. Of course, the precursor compound may be prepared and removed, purified, isolated, or stored from the vessel prior to the formation of the polycarbodiimide compound, if desired.

For efficiency, in certain embodiments, combining the precursor compound, the diisocyanate compound, and the carbodiimidization catalyst to form the reaction mixture is carried out at the desired temperature. This allows for the method to be carried out at a constant setpoint temperature. Alternatively, the reaction mixture may be formed at room temperature and subsequently heated to the first temperature.

Heating the reaction mixture at the first temperature may be carried out in the presence of a solvent or in the absence of a solvent. If desired, suitable solvents include organic solvents, such as toluene, xylene, tetrahydrofuran, etc. However, in certain embodiments, heating the reaction mixture is carried out in the absence of any solvent other than the precursor compound, the carbodiimidization catalyst, the diisocyanate compound, and optionally the stabilizing agent.

As introduced above, the reaction mixture is heated at the first temperature for the first period of time. The first period of time during which the reaction mixture is heated at the first temperature is generally sufficient for the reaction mixture to precipitate, gel, and/or become turbid. For example, the reaction mixture is typically a transparent (i.e., optically clear) liquid having a yellow hue. However, the first period of time is sufficient for the reaction mixture to precipitate, gel, and/or become turbid. Generally, turbidity of the reaction mixture increases with time, i.e., turbidity and time are directly proportional. Said differently, the reaction mixture typically becomes more turbid as time progresses. The reaction mixture may have various degrees of turbidity without departing from the scope of the present invention. Similarly, the first period of time is not limited to the period of time necessary for the reaction mixture to become slightly turbid. Rather, the first period of time may extend beyond the period of time necessary for the reaction mixture to become slightly turbid. Said differently, the first period of time may be selected such that the reaction mixture is heated at the first temperature even after the reaction mixture precipitates, gels, and/or becomes turbid without departing from the scope of the present invention.

The step of heating the reaction mixture is typically carried out in an inert atmosphere, i.e., an atmosphere substantially free from oxygen. Any inert atmosphere known in the art may be utilized during the step of heating the reaction mixture. Typically, the inert atmosphere comprises an inert gas, such as nitrogen, argon, helium, and carbon dioxide, etc.

As readily understood in the art, carbon dioxide gas is released during the step of heating the reaction mixture, which is generally associated with the formation of the polycarbodiimide polymer. Specifically, carbon dioxide is a by-product formed when —N═C═O groups present in the isocyanate component react with one another to form —N═C═N— linkages.

A reaction scheme illustrative of the polymerization of the diisocyanate compound is set forth below. In the reaction scheme below, the diisocyanate compound comprises 2,4-toluene diisocyanate (2,4-TDI), which is reacted in the presence of a carbodiimidization catalyst to produce various polycarbodiimide backbones. In the polycarbodiimide backbones of the reaction scheme below, n is an integer dependent upon the molecular weight of the particular polycarbodiimide. The precursor compound generally caps the terminal isocyanate groups to form the polycarbodiimide polymer.

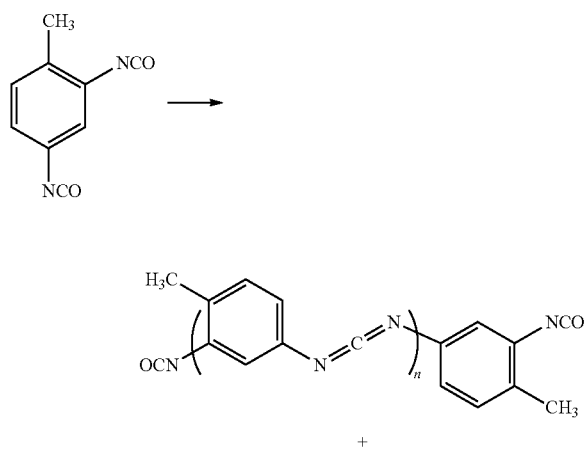

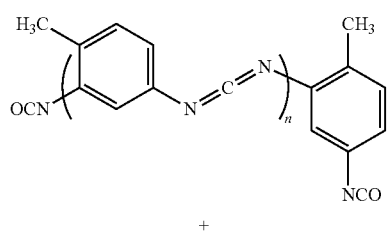

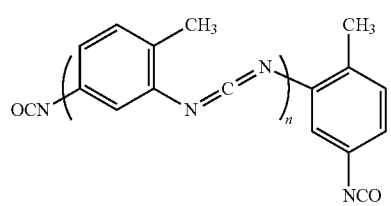

It is to be appreciated that the reaction scheme above relates solely to the polymerization of the diisocyanate compound, whereas in the instant method, the diisocyanate compound is reacted with and in the presence of the precursor compound.

In various embodiments, the first period of time is from greater than 0 to 18, alternatively from greater than 0 to 12, alternatively from 1 to 10, alternatively from 2 to 8, hours. The first period of time may vary from these ranges contingent on various factors, such as the particular precursor compound utilized, the first temperature at which the reaction mixture is heated, etc.

The structure of the polycarbodiimide polymer is contingent on the precursor compound utilized. In particular, as introduced above, the precursor compound generally caps the polycarbodiimide polymer. As such, the end caps of the polycarbodiimide polymer are generally the sub-units of the precursor compound, particularly when the precursor compound is the dimer.

For example, in one specific embodiment when the precursor compound comprises the carbodiimide compound (and, in this case, a diphenylcarbodiimide compound), and the diisocyanate compound comprises TDI (and, in this case, 2,4-TDI), the polycarbodiimide may have the following structure, which is for illustrative purposes only:

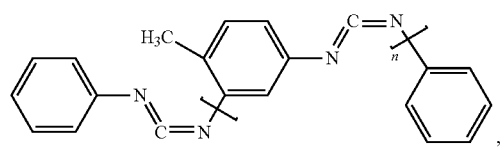

where subscript n represents the number of repeating units in the polycarbodiimide polymer. Alternatively, in one specific embodiment when the precursor compound comprises the urethane compound, and the diisocyanate compound comprises 2,4-TDI, the polycarbodiimide may have the following structure, which is for illustrative purposes only:

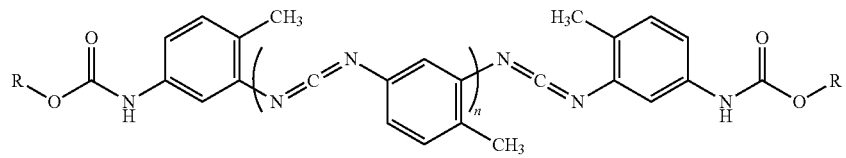

where each R is an independently selected organic group based on the particular alcohol utilized to form the precursor compound, and subscript n represents the number of repeating units in the polycarbodiimide polymer.

If desired the resulting polycarbodiimide polymer may be isolated, dissolved in a solvent, incorporated into a composition, etc.

Additional examples of further components that may be present along with the polycarbodiimide in composition form include adhesion promoters, UV stabilizers, colorants, flame retardants, fillers, thixotropic agents, diluents, etc.

The polycarbodiimide polymer formed via the method may be utilized in various and diverse industries. For example, the polycarbodiimide polymer may be utilized in electrical and electronic packaging applications. Examples of electrical and electronic packaging applications in which the polycarbodiimide polymer may be utilized include wire and cable tapes; insulation for coils, magnet wire, transformers, and capacitors; substrates for flexible printed circuits; films for photovoltaic cells; and magnetic and pressure-sensitive tapes. The polycarbodiimide polymer may also be utilized in synthetic fiber applications. Additionally, the polycarbodiimide polymer may be utilized in the automotive and aerospace industry. For example, the polycarbodiimide polymer may be utilized in under-the-hood applications in view of its excellent heat resistance. Similarly, the polycarbodiimide polymer may be utilized in o-ring seals and gaskets, or may be utilized in fuel lines. Further, the polycarbodiimide polymer may be utilized in coating compositions and/or inks.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The following examples are intended to illustrate the invention and are not to be viewed in any way as limiting to the scope of the invention.

EXAMPLES

The following components are referenced throughout the Examples:
Diisocyanate Compound is toluene diisocyanate (TDI).
Initial Compound 1 is phenyl isocyanate; and
Initial Compound 2 is n-hexanol;
Initial Compound 3 is n-decanol;
Precursor Compound 1 has the general formula:

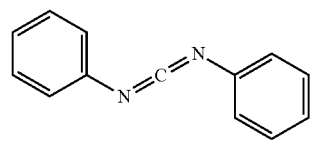

Precursor Compound 2 has the general formula:

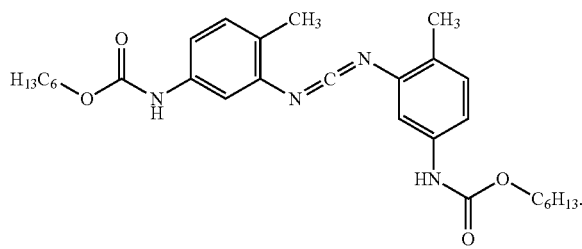

Precursor Compound 3 has the general formula:

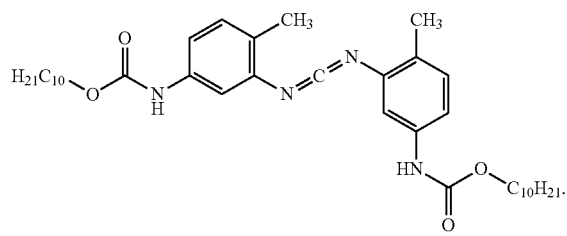

Solvent is xylene;
Stabilizing Agent is triphenylphosphite.
Carbodiimidization Catalyst is 3-methyl-1-phenyl-2-phospholene-1-oxide.

Example 1

25.13 grams of Initial Compound 1 are disposed in a dried 3-neck 100 mL round bottom flask under a steady stream of nitrogen. The flask is equipped with a condenser and stir bar and the temperature of the flask is increased from ambient temperature to about 106° C. Nitrogen is bubbled into the liquid, and 0.05 grams of the Carbodiimidization Catalyst and 0.05 grams of the Stabilizing Agent are disposed into the flask. The contents of the flask are stirred at 106° C. for 90 minutes to form Precursor Compound 1. 24.87 grams of Diisocyanate Compound are disposed in the flask while the contents of the flask, i.e., the Precursor Compound, are heated at 106° C. The addition of the Diisocyanate Compound results in the formation of a reaction mixture in the flask. Rapid bubbling is observed in the reaction mixture, which is attributable to the formation of carbon dioxide. The contents of the flask have a temperature less than 100° C. due to the addition of the Diisocyanate Compound, which is utilized at ambient temperature. The flask is continuously heated at 106° C. GPC and IR analyses of the reaction mixture are recorded every hour for 6 hours. After 4 hours, there was no change in the IR spectra, meaning the reaction had been carried out through completion. A polycarbodiimide polymer results in the reaction product, which is a golden viscous liquid.

Example 2

369.0 grams of Initial Compound 1 are disposed in a dried 4-neck 1 L round bottom flask under a steady stream of nitrogen. The flask is equipped with a condenser, a mechanical stirrer, and a thermocouple. The temperature of the contents of the flask is increased from ambient temperature to about 106° C. Nitrogen is bubbled into the liquid, and 1.5 grams of the Carbodiimidization Catalyst and 1.5 grams of the Stabilizing Agent are disposed into the flask. The temperature of the flask increases to about 112° C. because of the exothermic reaction associated with the formation of Precursor Compound 1 from Initial Compound 1. The contents of the flask are stirred at 106° C. for 60 minutes to form Precursor Compound 1. An IR measurement after 60 minutes confirms that the NCO groups of the Initial Compound 1 are consumed. 628.0 grams of Diisocyanate Compound are disposed in the flask while the contents of the flask, i.e., the Precursor Compound, are heated at 106° C. The addition of the Diisocyanate Compound results in the formation of a reaction mixture in the flask. Rapid bubbling is observed in the reaction mixture, which is attributable to the formation of carbon dioxide. The contents of the flask have a temperature less than 100° C. due to the addition of the Diisocyanate Compound, which is utilized at ambient temperature. The flask is continuously heated at 106° C. GPC and IR analyses of the reaction mixture are recorded ever hour. After 3 hours, there was no change in the IR spectra, meaning the reaction had been carried out through completion. A polycarbodiimide polymer results in the reaction product, which is a translucent golden viscous liquid.

Example 3

9.87 grams of Initial Compound 2 and 35.0 grams of Diisocyanate Compound are disposed in a flame dried round bottom flask (250 mL) fitted with a stir bar, thermocouple, condenser, and nitrogen sparge. Initial Compound 2 is disposed in the flask prior to Diisocyanate Compound. Upon addition of the Diisocyanate Compound, the temperature of the flask increased (via exotherm) from room temperature to about 92° C. and returned to about room temperature after 1 hour. The contents of the flask were analyzed via IR after 40 minutes and after 3.5 hours, with no change in the IR spectra. As such, Precursor Compound 2 is formed in the flask from Initial Compound 2 and Diisocyanate Compound. 37.49 g of Solvent are disposed in the flask and the temperature is raised to about 90° C. 0.19 grams of Carbodiimidization Catalyst and 0.20 grams of Stabilizing Agent are disposed in the flask to form a reaction mixture. The temperature of the reaction mixture is raised to about 106° C. for 1 hour and allowed to continue to heat for an additional 3 hours. A polycarbodiimide polymer results in the reaction product.

Example 4

30.56 grams of Diisocyanate Compound are dissolved in 31.15 grams of Solvent (which was dried with MgSO$_4$) and disposed in a flame dried round bottom flask (250 mL) fitted with a stir bar, thermocouple, condenser, and nitrogen sparge. 32.38 grams of Initial Compound 2 are disposed in the flask at room temperature and stirred without an external heating source. The temperature of the flask increased (via exotherm) from room temperature to about 74° C. and returned to about room temperature after 1 hour. The contents of the flask form an opaque viscous white solution, attributable to the formation of Precursor Compound 2 in the flask. 0.19 grams of Carbodiimidization Catalyst and 0.20 grams of Stabilizing Agent are disposed in the flask to form a reaction mixture. The temperature of the reaction mixture is raised to about 120° C. under stirring overnight before cooling to room temperature. A polycarbodiimide polymer in the form of a low viscosity fluid results in the reaction product.

Example 5

55.25 grams of Diisocyanate Compound are dissolved in 31.30 grams of Solvent (which was dried with MgSO$_4$) and disposed in a flame dried round bottom flask (250 mL) fitted with a stir bar, thermocouple, condenser, and nitrogen sparge. 32.35 grams of Initial Compound 2 are disposed in the flask at room temperature and stirred without an external heating source. The temperature of the flask increased (via exotherm) from room temperature to about 96° C. and returned to about room temperature after 1 hour. The contents of the flask were stirred overnight at room temperature, and the formation of Precursor Compound 2 from the Initial Compound 2 in the flask is confirmed via IR. The flask is heated at 120° C. and the temperature of the contents of the flask slowly increases. When the contents of the flask reach 105° C., 0.20 grams of the Carbodiimidization Catalyst and 0.19 grams of the Stabilizing Agent are disposed in the flask to form a reaction mixture. The reaction mixture is heated at 120° C. under stirring for 1 hour, after which the reaction product has a slight yellow hue. The reaction mixture is heated at 120° C. under stirring for an additional 7 hours, at which point IR confirmed the presence of a nominal amount of NCO in the reaction mixture. There is little change in the IR spectra after an additional 1 hour of heating. An additional 5.77 grams of Diisocyanate Compound are added to the reaction mixture at 120° C. After 1 hour, the NCO stretch was nearly undetectable via IR. The reaction mixture is heated at 120° C. for an additional 4 hours. A polycarbodiimide polymer in the form of a slightly yellow tacky solid results.

Example 6

25.55 grams of Diisocyanate Compound are disposed in a flame dried round bottom flask (250 mL) fitted with a stir bar, thermocouple, condenser, and nitrogen sparge. 23.34 grams of Initial Compound 3 are slowly disposed in the flask at room temperature and stirred without an external heating source. 62.50 grams of Solvent are disposed in the flask immediately after the Initial Compound 3 so as to control exotherm temperature in the flask. The temperature increases to about 60° C. and returns to room temperature. After about 2 hours, Precursor Compound 3 is formed in the flask from Initial Compound 3. The temperature of the flask is raised to 120° C. 0.21 grams of Carbodiimidization Catalyst and 0.18 grams of Stabilizing Agent are disposed in the flask to form a reaction mixture. The temperature of the reaction mixture is raised to about 140° C. under stirring for 4 hours. Another 44.49 grams of the Diisocyanate Compound is disposed in the reaction mixture and the reaction mixture is heated for an additional 3 hours at 140° C. No residual NCO groups are detected in the reaction mixture via IR. A polycarbodiimide polymer results in the reaction product.

Example 7

31.23 grams of Initial Compound 1, 0.46 grams of Carbodiimidization Catalyst and 0.46 grams of Stabilizing Agent are disposed at room temperature in a 100 mL 4-neck round bottom flask fitted with a stir bar, thermocouple, condenser, and nitrogen sparge. The contents of the flask are heated gradually to about 140° C., although the temperature reached about 148° C. prior to returning to 140° C. after 30 min. IR spectra shows nearly complete consumption of NCO groups in the Initial Compound 1 after 30 minutes. 14.25 grams of Diisocyanate Compound are disposed in the flask, and the contents of the flask are heated for another 30 min at 140° C. IR spectra show nearly complete consumption of NCO groups upon formation of a polycarbodiimide polymer.

Comparative Example 1

492 grams of Diisocyanate Compound and 1.00 grams of Stabilizing Agent are disposed in a 2 L 3-neck round bottom flask at room temperature. The contents of the flask are heated to about 74° C., at which time 1.00 grams of Carbodiimidization Catalyst and Initial Compound are disposed in the flask with agitation. The contents of the flask are heated to 106° C. over time (roughly 30 minutes from initial heating). IR spectra are measured 1 hour after addition of the Carbodiimidization Catalyst and every hour thereafter. The reaction mixture became gray after the first hour of heating at 106° C. The contents of the flask are heated at 106° C. for 6.5 hours, after which the reaction mixture is cooled overnight. The reaction mixture has an amber color. The resulting polycarbodiimide has significant molecular weight distribution and undesirable byproducts.

Comparative Example 2

Comparative Example 2 corresponds to Example A of U.S. Pat. No. 5,572,083. In particular, 9.43 grams of Diisocyanate Compound, 9.43 grams of Initial Compound 1, 3.11 grams of Carbodiimidization Catalyst (10% in Solvent) and 27.0 grams of amyl acetate are disposed at room temperature in a 100 mL 4-neck round bottom flask. The contents of the flask are heated to about 140° C. over a period of 33 minutes, at which point the reaction is allowed to progress for another 30 minutes. IR spectra show nearly complete consumption of NCO groups upon formation of a polycarbodiimide polymer, which has significant molecular weight distribution.

Table 1 below illustrates the Mn, Mw, and polydispersity (PD) for each of the polycarbodiimide polymers of the Examples above. Mn and Mw are generally measured by gel permeation chromatography (GPC) columns calibrated via polystyrene standards. The Mn and Mw values below are in Daltons.

TABLE 1

| Example | Mn | Mw | PD |
| --- | --- | --- | --- |
| Example 1 | 220 | 780 | 3.55 |
| Example 2 | 1350 | 8480 | 6.28 |
| Example 3 | 870 | 4400 | 5.06 |
| Example 4 | 530 | 4190 | 7.91 |
| Example 5 | 640 | 1090 | 1.7 |
| Example 6 | 240 | 2120 | 8.83 |
| Example 7 | 1170 | 3940 | 3.37 |
| Comparative Example 1 | 485 | 1100 | 2.27 |
| Comparative Example 2 | 900 | 2280 | 2.53 |

The invention has been described in an illustrative manner, and it is to be understood that the terminology which has been used is intended to be in the nature of words of description rather than of limitation. Obviously, many modifications and variations of the present invention are possible in light of the above teachings. The invention may be practiced otherwise than as specifically described.

What is claimed is:
1. A method of producing a polycarbodiimide polymer, said method comprising the steps of:
preparing a precursor compound from a monofunctional isocyanate compound at a desired temperature such that the precursor compound is heated at the desired temperature upon formation;
combining the precursor compound, a diisocyanate compound, and a carbodiimidization catalyst to form a reaction mixture; and
heating the reaction mixture for a first period of time at a first temperature, thereby reacting the precursor com- pound and the diisocyanate compound in the presence of the carbodiimidization catalyst to produce the polycarbodiimide polymer, wherein the precursor compound contains a single carbodiimide bond, and wherein the monofunctional isocyanate is synthesized by reaction of a difunctional isocyanate with a monofunctional alcohol, a monofunctional thiol, or a monofunctional amine.

2. A method as set forth in claim 1, wherein the monofunctional isocyanate compound is selected from

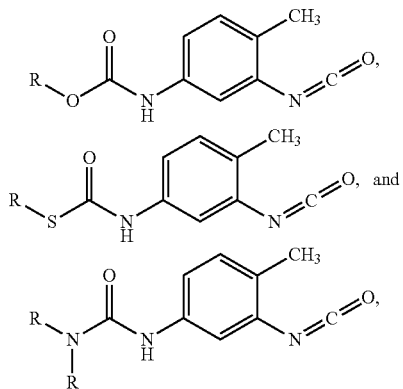

wherein each R is independently a hydrocarbyl group having from 1 to 20 carbon atoms.

3. A method as set forth in claim 1, wherein the precursor compound is prepared in the presence of the carbodiimidization catalyst.

4. A method as set forth in claim 1, wherein said diisocyanate compound comprises an aromatic diisocyanate.

5. A method as set forth in claim 1, wherein said diisocyanate compound has an ortho-substituted isocyanate group.

6. A method as set forth in claim 1, wherein said diisocyanate compound comprises toluene diisocyanate.

7. A method as set forth in claim 1, wherein combining the precursor compound, said diisocyanate compound, and the carbodiimidization catalyst to form the reaction mixture is carried out at the desired temperature.

8. A method as set forth in claim 1, wherein the desired temperature is from 70 to 150° C.

9. A method as set forth in claim 1, wherein the first temperature is from 70 to 150° C.

10. A method as set forth in claim 1, wherein a stabilizing agent is added to the reaction mixture.

11. A method as set forth in claim 10, wherein the stabilizing agent is selected from triphenylphosphite, 2,6-di-tert-butyl-4-methylphenol, and a combination thereof.

12. A method as set forth in claim 1, which is carried out in the absence of any solvent other than the precursor compound and said diisocyanate compound.

13. A method as set forth claim 1, wherein the carbodiimidization catalyst comprises a phospholene compound.

14. A method as set forth in claim 1, wherein the first period of time is from greater than 0 to 18 hours.

15. A method as set forth in claim 1, wherein the precursor compound is selected from:

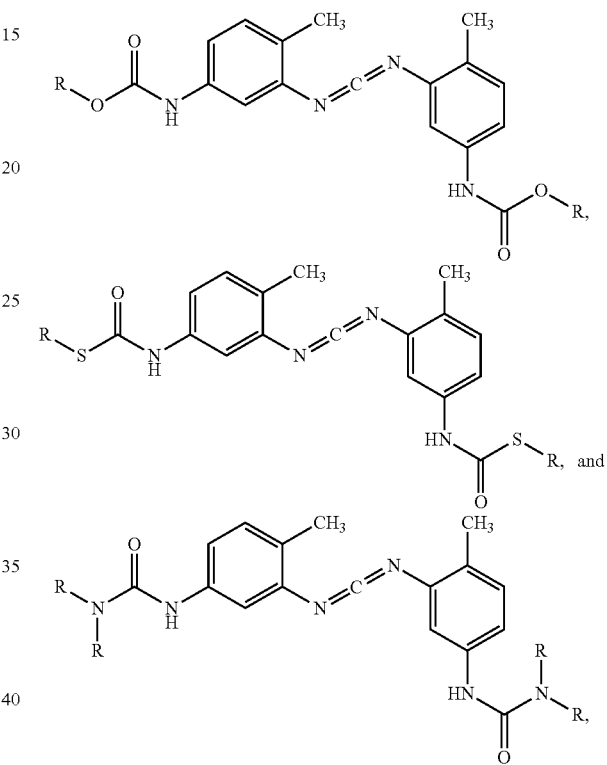

wherein each R is independently a hydrocarbyl group having from 1 to 20 carbon atoms.

16. A method as set forth in claim 1, wherein the step of preparing the precursor compound is carried out in the absence of said diisocyanate compound.

17. A method as set forth in claim 1, which is carried out in a single reaction vessel.

* * * * *